(12) United States Patent
Danek et al.

(10) Patent No.: US 7,740,017 B2
(45) Date of Patent: *Jun. 22, 2010

(54) METHOD FOR TREATING AN ASTHMA ATTACK

(75) Inventors: Christopher J. Danek, San Carlos, CA (US); Bryan E. Loomas, Los Gatos, CA (US); Thomas Keast, Sunnyvale, CA (US); Michael D. Laufer, Menlo Park, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 800 days.

This patent is subject to a terminal disclaimer.

(21) Appl. No.: 11/117,905

(22) Filed: Apr. 29, 2005

(65) Prior Publication Data

US 2005/0187579 A1 Aug. 25, 2005

Related U.S. Application Data

(63) Continuation of application No. 09/999,851, filed on Oct. 25, 2001, now Pat. No. 7,027,869, which is a continuation-in-part of application No. 09/535,856, filed on Mar. 27, 2000, now Pat. No. 6,634,363, and a continuation-in-part of application No. 09/296,040, filed on Apr. 21, 1999, now Pat. No. 6,411,852, which is a continuation-in-part of application No. 09/095,323, filed on Jun. 10, 1998, application No. 11/117,905, filed on Apr. 29, 2005, which is a continuation-in-part of application No. 09/436,455, filed on Nov. 8, 1999, now Pat. No. 7,425,212, and a continuation-in-part of application No. 10/232,909, filed on Aug. 30, 2002, now Pat. No. 7,556,624, which is a continuation of application No. 09/349,715, filed on Jul. 8, 1999, now Pat. No. 6,488,673, which is a continuation-in-part of application No. 09/260,401, filed on Mar. 1, 1999, now Pat. No. 6,283,988, which is a continuation-in-part of application No. 09/003,750, filed on Jan. 7, 1998, now Pat. No. 5,972,026, which is a continuation-in-part of application No. 08/833,550, filed on Apr. 7, 1997, now Pat. No. 6,273,907.

(51) Int. Cl.
*A61B 19/00* (2006.01)
*A61F 7/00* (2006.01)

(52) U.S. Cl. .......................... 128/898; 607/42; 607/96; 607/101

(58) Field of Classification Search ................... 607/42, 607/96–105, 124; 606/2, 13, 27, 28, 32, 606/41; 128/898
See application file for complete search history.

(56) References Cited

U.S. PATENT DOCUMENTS 1,155,169 A 9/1915 Starkweather (Continued)

FOREIGN PATENT DOCUMENTS

DE 19529634 A1 2/1997

(Continued)

OTHER PUBLICATIONS

Co-pending U.S. Appl. No. 09/244173.

(Continued)

*Primary Examiner*—Ahmed M Farah
(74) *Attorney, Agent, or Firm*—Perkins Coie LLP

(57) ABSTRACT

A method for treating the lung during an acute episode of reversible chronic obstructive pulmonary disease such as an asthma attack. The method comprises transferring energy to an airway wall of an airway such that a diameter of the airway is increased. The energy may be transferred to the airway wall prior to, during or after an asthma attack. The energy may be transferred in an amount sufficient to temporarily or permanently increase the diameter of the airway. The method may be performed while the airway is open, closed or partially closed.

7 Claims, 3 Drawing Sheets

U.S. PATENT DOCUMENTS

| | | |
|---|---|---|
| 1,207,479 A | 12/1916 | Bisgaard |
| 2,072,348 A | 3/1937 | Smith |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,116,589 A | 9/1978 | Rishton |
| 4,129,129 A | 12/1978 | Amrine |
| 4,461,283 A | 7/1984 | Doi |
| 4,502,490 A | 3/1985 | Evans et al. |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,772,112 A | 9/1988 | Zider et al. |
| 4,779,614 A | 10/1988 | Moise |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,920,978 A | 5/1990 | Colvin |
| 4,944,722 A | 7/1990 | Carriker et al. |
| 4,955,377 A | 9/1990 | Lennox et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,936 A | 4/1991 | Yamanaka et al. |
| 5,019,075 A | 5/1991 | Spears et al. |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,107,830 A | 4/1992 | Younes |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,167,223 A | 12/1992 | Koros et al. |
| 5,170,803 A | 12/1992 | Hewson et al. |
| 5,174,288 A | 12/1992 | Bardy et al. |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,293,869 A | 3/1994 | Edwards et al. |
| 5,309,910 A | 5/1994 | Edwards et al. |
| 5,313,943 A | 5/1994 | Houser et al. |
| 5,345,936 A | 9/1994 | Pomeranz et al. |
| 5,368,591 A | 11/1994 | Lennox et al. |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,425,811 A | 6/1995 | Mashita |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,478,309 A | 12/1995 | Sweezer et al. |
| 5,496,311 A | 3/1996 | Abele et al. |
| 5,500,011 A | 3/1996 | Desai |
| 5,505,728 A | 4/1996 | Ellman et al. |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,549,559 A | 8/1996 | Eshel |
| 5,549,655 A | 8/1996 | Erickson |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,578,072 A | 11/1996 | Barone et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,624,439 A | 4/1997 | Edwards et al. |
| 5,626,618 A | 5/1997 | Ward et al. |
| 5,630,425 A | 5/1997 | Panescu et al. |
| 5,634,471 A | 6/1997 | Fairfax et al. |
| 5,641,326 A | 6/1997 | Adams |
| 5,647,870 A | 7/1997 | Kordis et al. |
| 5,678,535 A | 10/1997 | DiMarco |
| 5,680,860 A | 10/1997 | Imran |
| 5,681,308 A | 10/1997 | Edwards et al. |
| 5,693,078 A | 12/1997 | Desai et al. |
| 5,699,799 A | 12/1997 | Xu et al. |
| 5,707,218 A | 1/1998 | Maher et al. |

| | | | | | | |
|---|---|---|---|---|---|---|
| 5,707,336 A | 1/1998 | Rubin | | 5,992,419 A | 11/1999 | Sterzer et al. |
| 5,707,352 A | 1/1998 | Sekins et al. | | 5,993,462 A | 11/1999 | Pomeranz et al. |
| 5,722,401 A | 3/1998 | Pietroski et al. | | 5,999,855 A | 12/1999 | DiMarco |
| 5,722,403 A | 3/1998 | McGee et al. | | 6,004,269 A | 12/1999 | Crowley et al. |
| 5,722,416 A | 3/1998 | Swanson et al. | | 6,009,877 A | 1/2000 | Edwards |
| 5,725,525 A | 3/1998 | Kordis | | 6,010,500 A | 1/2000 | Sherman et al. |
| 5,727,569 A | 3/1998 | Benetti et al. | | 6,016,437 A | 1/2000 | Tu et al. |
| 5,730,128 A | 3/1998 | Pomeranz et al. | | 6,024,740 A | 2/2000 | Lesh et al. |
| 5,730,726 A | 3/1998 | Klingenstein | | 6,036,687 A | 3/2000 | Laufer et al. |
| 5,730,741 A | 3/1998 | Horzewski et al. | | 6,045,550 A | 4/2000 | Simpson et al. |
| 5,740,808 A | 4/1998 | Panescu et al. | | 6,053,172 A | 4/2000 | Hovda et al. |
| 5,741,248 A | 4/1998 | Stern et al. | | 6,071,280 A | 6/2000 | Edwards et al. |
| 5,752,518 A | 5/1998 | McGee et al. | | 6,071,281 A | 6/2000 | Burnside et al. |
| 5,755,714 A | 5/1998 | Murphy-Chutorian | | 6,083,255 A * | 7/2000 | Laufer et al. ............ 607/96 |
| 5,755,753 A | 5/1998 | Knowlton | | 6,092,528 A | 7/2000 | Edwards |
| 5,759,158 A | 6/1998 | Swanson | | 6,142,993 A | 11/2000 | Whayne et al. |
| 5,765,568 A | 6/1998 | Sweezer, Jr. et al. | | 6,152,899 A | 11/2000 | Farley et al. |
| 5,769,846 A | 6/1998 | Edwards et al. | | 6,198,970 B1 | 3/2001 | Freed et al. |
| 5,772,590 A | 6/1998 | Webster, Jr. | | 6,200,333 B1 * | 3/2001 | Laufer .................. 607/96 |
| 5,779,698 A | 7/1998 | Clayman et al. | | 6,254,598 B1 | 7/2001 | Edwards et al. |
| 5,782,239 A | 7/1998 | Webster, Jr. | | 6,273,907 B1 * | 8/2001 | Laufer .................. 607/96 |
| 5,782,797 A | 7/1998 | Schweich, Jr. et al. | | 6,283,988 B1 * | 9/2001 | Laufer et al. ........... 607/96 |
| 5,782,848 A | 7/1998 | Lennox | | 6,283,989 B1 | 9/2001 | Laufer et al. |
| 5,782,899 A | 7/1998 | Imran | | 6,299,633 B1 | 10/2001 | Laufer |
| 5,792,064 A | 8/1998 | Panescu et al. | | 6,338,836 B1 | 1/2002 | Kuth et al. |
| 5,795,303 A | 8/1998 | Swanson et al. | | 6,411,852 B1 * | 6/2002 | Danek et al. ............ 607/42 |
| 5,800,375 A | 9/1998 | Sweezer et al. | | 6,416,740 B1 | 7/2002 | Unger |
| 5,807,306 A | 9/1998 | Shapland et al. | | 6,423,105 B1 | 7/2002 | Iijima et al. |
| 5,810,757 A | 9/1998 | Sweezer, Jr. et al. | | 6,440,129 B1 | 8/2002 | Simpson |
| 5,810,807 A | 9/1998 | Ganz et al. | | 6,488,673 B1 | 12/2002 | Laufer et al. |
| 5,817,073 A | 10/1998 | Krespi | | 6,634,363 B1 * | 10/2003 | Danek et al. ............ 128/898 |
| 5,820,554 A | 10/1998 | Davis et al. | | 7,027,869 B2 * | 4/2006 | Danek et al. ............ 607/42 |
| 5,827,277 A | 10/1998 | Edwards | | 7,104,987 B2 | 9/2006 | Biggs et al. |
| 5,833,651 A | 11/1998 | Donovan et al. | | 7,198,635 B2 * | 4/2007 | Danek et al. ............ 607/96 |
| 5,836,947 A | 11/1998 | Fleischman et al. | | 7,264,002 B2 * | 9/2007 | Danek et al. ............ 128/898 |
| 5,843,075 A | 12/1998 | Taylor | | 7,425,212 B1 * | 9/2008 | Danek et al. ............ 606/47 |
| 5,843,077 A | 12/1998 | Edwards | | 2002/0091379 A1 | 7/2002 | Danek et al. |
| 5,846,238 A | 12/1998 | Jackson et al. | | 2003/0159700 A1 | 8/2003 | Laufer et al. |
| 5,848,969 A | 12/1998 | Panescu et al. | | 2003/0233099 A1 | 12/2003 | Danaek et al. |
| 5,848,972 A | 12/1998 | Triedman et al. | | 2004/0031494 A1 | 2/2004 | Danek et al. |
| 5,849,026 A | 12/1998 | Zhou et al. | | 2004/0182399 A1 | 9/2004 | Danek et al. |
| 5,855,577 A | 1/1999 | Murphy-Chutorian et al. | | 2005/0010270 A1 | 1/2005 | Laufer |
| 5,860,974 A | 1/1999 | Abele | | 2005/0171396 A1 | 8/2005 | Pankratov et al. |
| 5,863,291 A | 1/1999 | Schaer | | 2007/0106296 A1 * | 5/2007 | Laufer et al. ............ 606/50 |
| 5,865,791 A | 2/1999 | Whayne et al. | | | | |
| 5,868,740 A | 2/1999 | LeVeen et al. | | | | |
| 5,871,443 A | 2/1999 | Edwards et al. | | | FOREIGN PATENT DOCUMENTS | |
| 5,871,523 A | 2/1999 | Fleischman et al. | | | | |
| 5,873,865 A | 2/1999 | Horzewski et al. | | EP | 189329 A3 | 6/1987 |
| 5,881,727 A | 3/1999 | Edwards | | EP | 286145 A3 | 10/1990 |
| 5,882,346 A | 3/1999 | Pomeranz et al. | | EP | 282225 B1 | 6/1992 |
| 5,891,136 A | 4/1999 | McGee et al. | | EP | 908713 A1 | 4/1999 |
| 5,897,554 A | 4/1999 | Chia et al. | | EP | 908150 B1 | 5/2003 |
| 5,899,882 A | 5/1999 | Waksman et al. | | EP | 768091 B1 | 7/2003 |
| 5,904,651 A | 5/1999 | Swanson et al. | | FR | 2659240 B1 | 7/1997 |
| 5,904,711 A | 5/1999 | Flom et al. | | GB | 2233293 | 2/1994 |
| 5,908,445 A | 6/1999 | Whayne et al. | | RU | 2091054 C1 | 9/1997 |
| 5,908,446 A | 6/1999 | Imran | | SU | 545358 T | 2/1977 |
| 5,911,218 A | 6/1999 | DiMarco | | WO | WO-9733715 A1 | 9/1997 |
| 5,919,172 A | 7/1999 | Golba, Jr. | | WO | WO-9737715 A1 | 10/1997 |
| 5,935,079 A | 8/1999 | Swanson et al. | | WO | WO-9844854 A1 | 10/1998 |
| 5,941,869 A | 8/1999 | Patterson et al. | | WO | WO-9856234 A1 | 12/1998 |
| 5,951,546 A | 9/1999 | Lorentzen | | WO | WO-9856324 A1 | 12/1998 |
| 5,954,661 A | 9/1999 | Greenspon et al. | | WO | WO-9858681 A3 | 12/1998 |
| 5,954,662 A | 9/1999 | Swanson et al. | | WO | WO-9903413 A1 | 1/1999 |
| 5,957,961 A | 9/1999 | Maguire et al. | | WO | WO-9913779 A2 | 3/1999 |
| 5,964,753 A | 10/1999 | Edwards | | WO | WO-9934741 A1 | 7/1999 |
| 5,964,796 A | 10/1999 | Imran | | WO | WO-9944506 A1 | 9/1999 |
| 5,971,983 A | 10/1999 | Lesh | | WO | WO-9945855 A1 | 9/1999 |
| 5,972,026 A * | 10/1999 | Laufer et al. ............ 607/96 | | WO | WO-0051510 A1 | 9/2000 |
| 5,979,456 A | 11/1999 | Magovern | | WO | WO-0103642 A1 | 1/2001 |
| 5,984,917 A | 11/1999 | Fleischman et al. | | | | |
| 5,991,650 A | 11/1999 | Swanson et al. | | | | |

WO  WO-0232334 A1  4/2002

OTHER PUBLICATIONS

Co-pending U.S. Appl. No. 09/436455.
Co-pending U.S. Appl. No. 09/095323.
Simon R. Johnson et al., Synthetic Functions of Airway Smooth Muscle in Asthma, Trends Pharmacol. Sci., Aug. 1997, 18(8), 288-292.
Macklem P.T., Mechanical Factors Determining Maximum Bronchoconstriction, European Respiratory Journal, Jun. 1989, 6, 516s-519s.
James C. Hogg, The Pathology of Asthma, APMIS, Oct. 1997, 105(10), 735-745.
Dierkesmann et al., Indication and Results of Endobronchial Laser Therapy, Lung, 1990, 168, 1095-1102.
Netter F.H., Respiratory System: A Compilation of Paintings Depicting Anatomy and Embryology, Physiology, Pathology, Pathophysiology, and Clinical Features and Treatment of Diseases, In The CIBA Collection of Medical Illustrations M.B. Divertie, ed., Summit: New Jerse, 1979, vol. 7, 119-135.
Provotorov et al., The Clinical Efficacy of Treating Patients with Nonspecific Lung Disease by Using Low-energy Laser Irradiation and Intrapulmonary Drug Administration, ISSN: 0040-3660., Terapevticheskii Arkhiv (USSR), 1991, 63 (12), 18-23.
Vorotnev et al., Low energy laser treatment of chronic obstructive bronchitis in a general rehabilitation center, ISSN: 0040-3660., Terapevticheskil Arkhiv, 1997, 69 (3), 17-19.
Wiggs B.R. et al., On the Mechanism of Mucosal Folding in Normal and Asthmatic Airways, J. Appl. Physiol., Dec. 1997, 83(6), 1814-1821.
Ivaniuta O. M. et al., Effect Of Low-Power Laser Irradiation Of Bronchial Mucosa On The State Of Systemic And Local Immunity in Patients With Chronic Bronchitis, Problemy Tuberkuleza, 1991, 6, 26-29.
An, S.S et al., Airway smooth muscle dynamics: a common pathway of airway obstruction in asthma, European Respiratory Journal, 2007, vol. 29, No. 5, pp. 834-860.
Bel: E. H., Hot Stuff: Bronchial Thermoplasty for Asthma, American Journal of Respiratory and Critical Care Medicine, 2006, vol. 173, pp. 941-942.
Brown, R. H. et al., In vivo evaluation of the effectiveness of bronchial thermoplasty with computed tomography, Journal of Applied Physiology, 2005, vol. 98, pp. 1603-1606.
Brown, R. H. et al., Effect of bronchial thermoplasty on airway distensibility, European Respiratory Journal, vol. 26, No. 2, pp. 277-282.
Chhajed, P., Will There be a Role for Bronchoscopic Radiofrequency Ablation?, 2005, J Bronchol, vol. 12, No. 3, p. 184.
Cox, G., et al., Early Clinical Experience With Bronchial Thermoplasty for the Treatment of Asthma, 2002, p. 1068.
Cox, G. et al., Asthma Control During the Year After Bronchial Thermoplasty, The New England Journal of Medicine, Mar. 29, 2007, vol. 356, No. 13, pp. 1327-1337.
Cox, G. et al., Bronchial Thermoplasty: One-Year Update, American Thoracic Society Annual Meeting, 2004, p. 1.
Cox, G., et al., Development of a Novel Bronchoscopic Therapy for Asthma, Journal of Allergy and Clinical Immunology, 2003, p. 1.
Cox, G., et al., Bronchial Thermoplasty for Asthma, American Journal of Respiratory and Critical Care Medicine, 2006, vol. 173, pp. 965-969.
Cox, G., Bronchial Thermoplasty: Long-Term Follow-up and Patient Satisfaction, 2004, p. 1.
Cox, G., et al., Radiofrequency ablation of airway smooth muscle for sustained treatment of asthma: preliminary investigations, European Respiratory Journal, 2004, 24, pp. 659-663.
Cox, G., et al., Clinical Experience with Bronchial Thermoplasty for the Treatment of Asthma, 2003, Chest 124, p. 106S.
Cox, G., et al., Impact of bronchial thermoplasty on asthma status: interim results from the AIR trial, 2006, European Respiratory Society Annual Meeting, Munich, Germany, p. 1.
Danek, C. J., et al., Bronchial thermoplasty reduces canine airway responsiveness to local methacholine challenge, 2002, American Thoracic Society Annual Meeting, p. 1.
Danek, C. J., et al., Asthma Intervention Research (AIR) Trial Evaluation Bronchial Thermoplasty™: Early Results, 2002, American Thoracic Society Annual Meeting, p. 1.
Danek, C. J., et al., Reduction in airway hyperresponsiveness to methacholine by the application of RF energy in dogs, J Appl Physiol, 2004, vol. 97, pp. 1946-1953.
Solway, J. at al., Airway Smooth Muscle as a Target for Asthma Therapy, The New England Journal of Medicine, Mar. 29, 2007, 356(13), pp. 1367-1369.
Laviolette, et al., Asthma Invervention Research (AIR) Trial: Early Safety Assessment of Bronchial Thermoplasty, 2004, p. 1.
Leff, et al., Bronchial Thermoplasty Alters Airway Smooth Muscle and Reduces Responsiveness in Dogs: A Possible Procedure for the Treatment of Asthma, American Thoracic Society Annual Meeting, 2002, p. 1.
Lim, E. C. et al., Botulinum Toxin: A Novel Therapeutic Option for Bronchial Asthma?, Medicial Hypotheses, 2006, vol. 66, pp. 915-919.
Lombard, et al., Histologic Effects of Bronchial Thermoplasty of Canine and Human Airways, American Thoracic Society Annual Meeting, 2002, p. 1.
Mayse, M. et al., Clinical Pearls for Bronchial Thermoplasty, J Bronchol, Apr. 2007, vol. 14, No. 2, pp. 115-123.
Miller, J. D. et al., A Prospective Feasibility Study of Bronchial Thermoplasty in the Human Airway, 2005, vol. 127, No. 6, pp. 1999-2006.
Miller, J. D. et al., Bronchial Thermoplasty is Well Tolerated by Non-Asthmatic Patients Requiring Lobectomy, 2002, American Thoracic Society Annual Meeting, p. 1.
Rubin, et al. Bronchial Thermoplasty Improves Asthma Status of Moderate to Severe Peristent Asthmatics Over and Above Current Standard-of-Care, 2006, American College of Chest Physicians, 2 pages.
Wilson, S. R. et al., Global assessment after bronchial thermoplasty: the patients's perspective, Journal of Outcomes Research, 2006, vol. 10, pp. 37-46.
Sterk, P. J., Heterogeneity of Airway Hyperresponsiveness: Time for Unconventional, but Traditional Studies, 2004, The American Pshychological Society, pp. 2017-2018.
Toma, T. P., Brave New World for Interventional Bronchoscopy, 2005, Thorax, vol. 60, pp. 180-181.
Trow, T., Clinical Year in Review 1, proceedings of the American Thoracic Society, 2006, vol. 3, pp. 553-556.
Wizeman, et al., A Computer Model of Thermal Treatment of Airways by Radiofrequency (RF) Energy Delivery, 2007, American Thoracic Society Annual Meeting, p. 1.
Vasilotta, P. L. et al., "I-R Laser: A New Therapy in Rhino-Sino-Nasal Bronchial Syndrome with Asthmatic Component," American Society for Laser medicine and Surgery abstracts, date unknown, p. 74.

* cited by examiner

METHOD FOR TREATING AN ASTHMA ATTACK

CROSS REFERENCE TO RELATED APPLICATIONS

This application is:

(a) a continuation application of U.S. application Ser. No. 09/999,851 filed Oct. 25, 2001, now U.S. Pat. No. 7,027,869 B2, which is a continuation-in-part application of U.S. application Ser. No. 09/296,040 filed Apr. 21, 1999, now U.S. Pat. No. 6,411,852 B1, which is a continuation-in-part application of U.S. application Ser. No. 09/095,323 filed Jun. 10, 1998, each of which are herein incorporated by reference in their entirety;

(b) a continuation-in-part application of U.S. application Ser. No. 09/436,455 filed Nov. 8, 1999 now U.S. Pat. No. 7,425,212 which is incorporated by reference herein in its entirety; and (c) a continuation-in-part application of Ser. No. 10/232,909 filed on Aug. 30, 2002, now U.S. Pat. No. 7,556,624 which is a continuation of U.S. application Ser. No. 09/349,715 filed Jul. 8, 1999, and now U.S. Pat. No. 6,488,673 B1, which is a continuation-in-part of U.S. application Ser. No. 09/260,401 filed on Mar. 1, 1999, and now U.S. Pat. No. 6,283,988, which is a continuation-in-part application of U.S. application Ser. No. 09/003,750 filed Jan. 7, 1998, and now U.S. Pat. No. 5,972,026, which is a continuation-in-part application of U.S. application Ser. No. 08/833,550 filed Apr. 7, 1997, and now U.S. Pat. No. 6,273,907 B1.

U.S. application Ser. No. 09/999,851 is also a continuation-in-part application of U.S. application Ser. No. 09/535,856 filed on Mar. 27, 2000, and now U.S. Pat. No. 6,634,363, which is also incorporated by reference in its entirety.

BACKGROUND

Asthma is a serious chronic condition affecting an estimated 10 million Americans. Asthma is characterized by (i) bronchoconstriction, (ii) excessive mucus production, and (iii) inflammation and swelling of airways. These conditions cause widespread and variable airflow obstruction thereby making it difficult for the asthma sufferer to breathe. Asthma further includes acute episodes or attacks of additional airway narrowing via contraction of hyper-responsive airway smooth muscle. Other obstructive diseases such as COPD may also have a reversible component caused by one or more of the above mentioned three elements.

Asthma generally includes excessive mucus production in the bronchial tree. Usually, there is a general increase in bulk (hypertrophy) of the large bronchi and chronic inflammatory changes in the small airways. Excessive amounts of mucus are found in the airways and semisolid plugs of mucus may occlude some small bronchi. Also, the small airways are narrowed and show inflammatory changes. The reversible aspects of COPD include partial airway occlusion by excess secretions, and airway narrowing secondary to smooth muscle contraction, bronchial wall edema and inflammation of the airways.

In asthma, chronic inflammatory processes in the airway play a central role in increasing the resistance to airflow within the lungs. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Asthma is managed pharmacologically by: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management. Thus, current management techniques are neither completely successful nor free from side effects.

In view of the foregoing, a non-pharmacological asthma treatment which does not rely on avoiding stimuli is desirable.

SUMMARY OF THE INVENTION

The invention is a method for treating lung disease and in particular, a method for treating the lung during an acute episode of reversible obstructive pulmonary disease such as an asthma attack. One embodiment of the present invention includes a method for treating asthma comprising the step of transferring energy to an airway wall of an airway in a lung such that a diameter of the airway is increased. The energy may be transferred to the airway wall prior to, during or after an asthma attack. The energy may also be transferred in an amount sufficient to temporarily or permanently increase the effective diameter of the airway. The method may be performed while the airway is open, closed or partially closed.

In another embodiment of the invention, a method for treating asthma in a lung having a constricted airway comprises transferring energy to an airway wall of the constricted airway sufficient to open the airway. The energy transferred may be in an amount sufficient to permanently or temporarily open the constricted airway. The method may be performed to open a wholly constricted airway as well as a partly constricted airway.

In yet another variation of the invention, a method for treating lung disease comprises transferring energy to an airway wall to alter the airway wall in such a manner that a resistance to airflow of the airway is decreased. The method may be performed by transferring energy to increase the caliber of the airway. The airway wall may also be altered by decreasing a thickness of the airway wall. The energy may be transferred to the airway wall during an asthma attack.

In another variation of the invention, the method comprises manipulating a distal portion of an energy delivery apparatus to a first location along the airway prior to applying the energy. The energy delivering apparatus can include a rounded tip sufficiently flexible such that when the tip encounters a closed or partially closed airway, trauma to the airway is minimized. The energy is then applied to a discrete location while the distal portion of the energy delivery apparatus is stationary. The distal portion can then be moved to a new location and the process repeated until a number of discrete locations have been treated. In an alternative, the method comprises moving the distal portion of the energy delivery apparatus from the first location and applying energy while the distal portion is being moved in the airway.

In another variation of the present invention, a method comprises transferring energy to or from an airway wall to treat a lung disease such as asthma. The method may be carried out by inserting into the airway an apparatus having a cryogenic tip or other cooling means capable of transferring energy from the tissue, resulting in a desired condition such as a larger diameter airway.

In yet another variation of the invention, a combination of the above discussed techniques are carried out such that at one time, energy is applied while the distal portion of the energy delivery device is being moved and at another time, energy is applied when the distal portion of the apparatus is stationary.

BRIEF DESCRIPTION OF THE DRAWINGS

The invention will now be described in greater detail with reference to the various embodiments illustrated in the accompanying drawings wherein.

DETAILED DESCRIPTION

This invention relates to methods for improving airflow through the airways of a lung having reversible obstructive pulmonary disease. In accordance with the invention an airway may be treated during an acute episode of reversible obstructive pulmonary disease such as an asthma attack. The invention comprises applying or transferring energy to an airway wall to increase the diameter of the airway or otherwise reduce resistance to airflow through the airway. The energy may be transferred in an amount sufficient to temporarily or permanently increase the diameter of the airway. Notably, the method may be performed while the airway is open, closed or partially closed. The inventive method thus can "rescue" an asthma sufferer during an acute asthma episode by increasing the diameter of a constricted airway.

Figure 1:
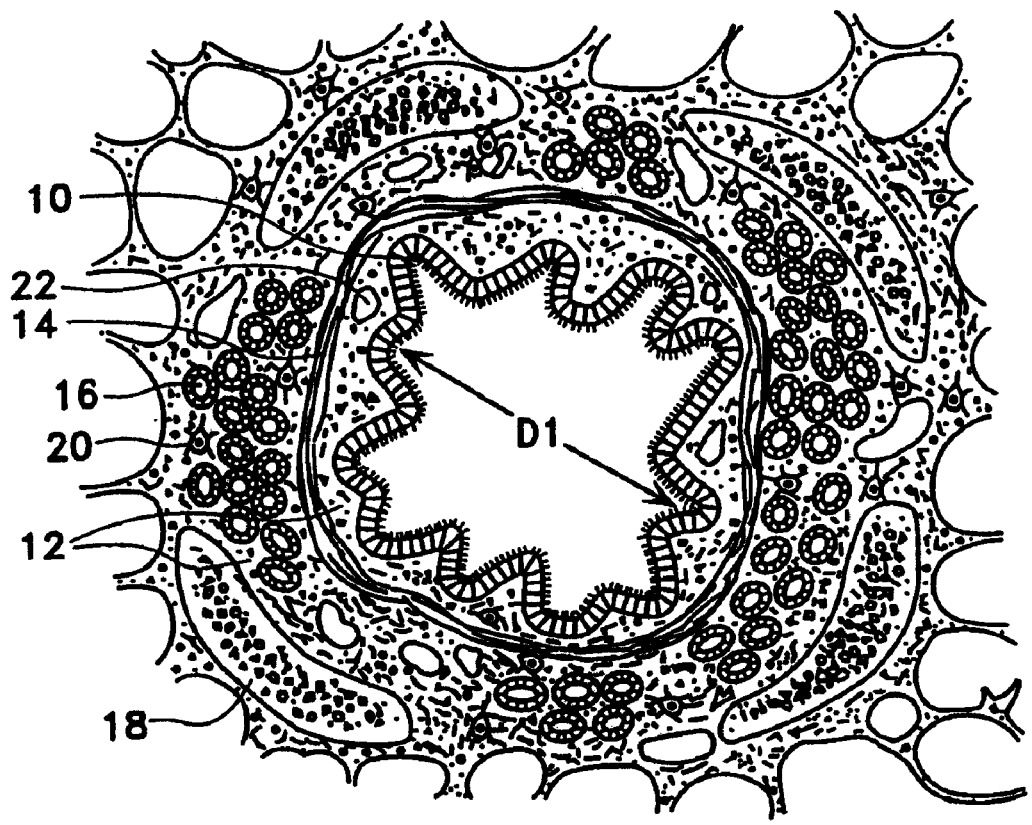
FIG. 1. is a cross sectional view of an airway in a healthy lung.
Figure 2:
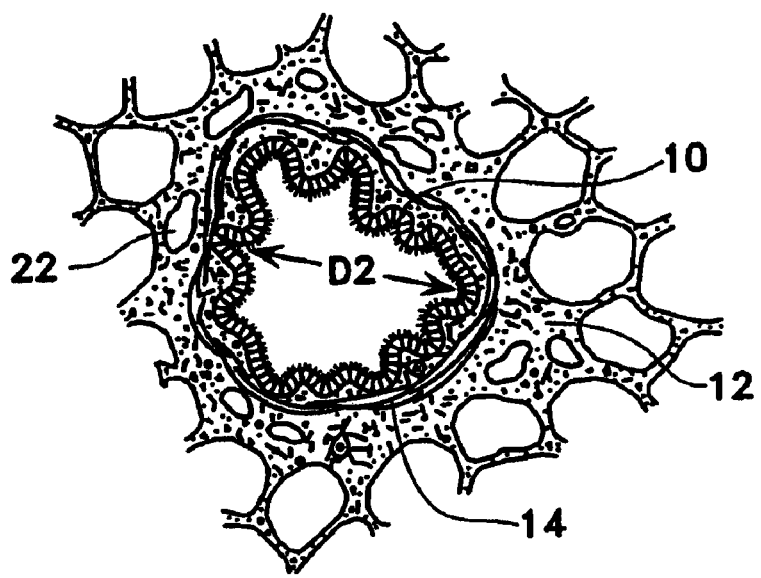
FIG. 2. shows a section through a bronchiole having an airway diameter smaller than that shown in FIG. 1.
Figure 3:
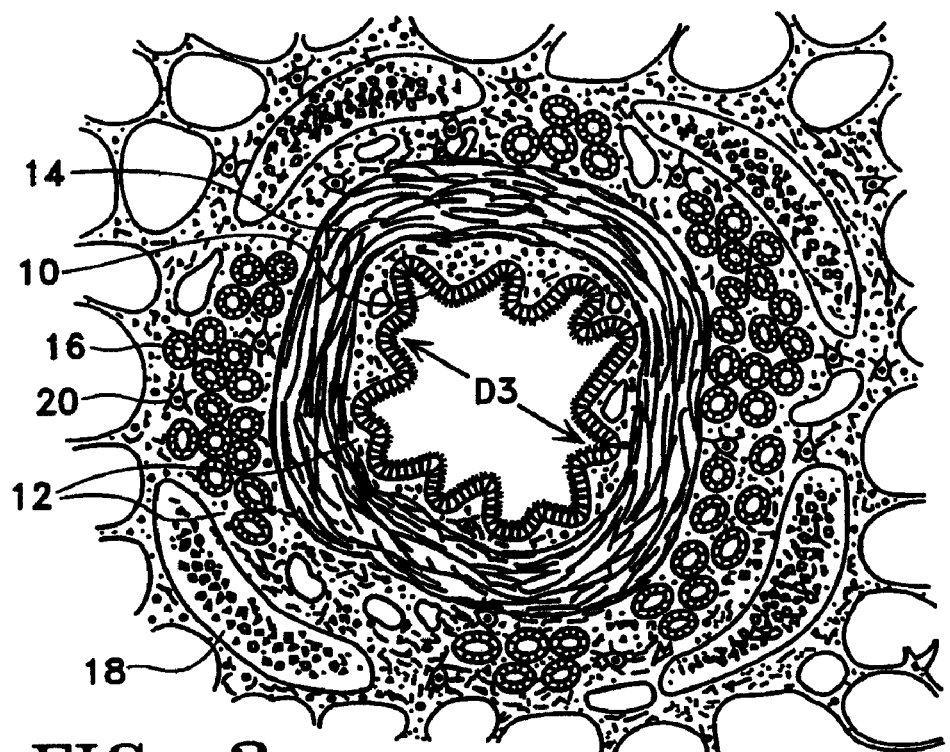
FIG. 3 illustrates the airway of FIG. 1 in which the smooth muscle has hypertrophied and increased in thickness causing reduction of the airway diameter.

Various airways are shown in FIGS. 1-3. FIGS. 1 and 2 show a cross section of two different airways in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 121 and smooth muscle tissue 14. The airway is thus quit different from other tissues such as blood vessel tissue which does not include such folds. The larger airways including the bronchus shown in FIG. 1 also have mucous glands 16 and cartilage 18 surrounding the smooth muscle tissue 14. Nerve fibers 20 and blood vessels 22 surround the airway.

FIG. 3 illustrates the bronchus of FIG. 1 in which the smooth muscle 14 has hypertrophied and increased in thickness causing the airway diameter to be reduced from the diameter D1 to a diameter D3. Accordingly, the airways to be treated with the device of the present invention may be 1 mm in diameter or greater. The airways to be treated are often second to eighth generation, and more preferably airways of the second to sixth generation.

Figure 4:
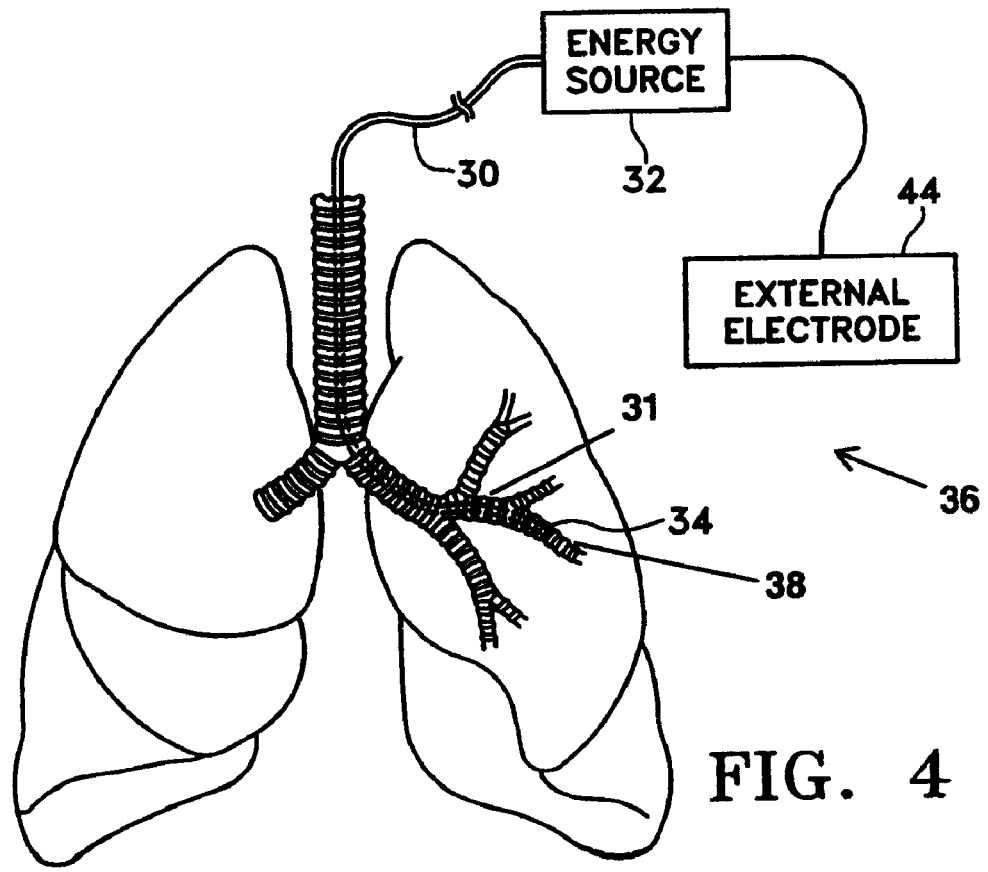
FIG. 4 is a schematic side view of the lungs being treated with a treatment device as described herein.

FIG. 4 is an illustration of the lungs being treated with a system 36 which can be used to carry out the present invention. The system 36 includes a controller 32 and an energy treatment device 30 which may be an elongated member as described further below. The device 30 also includes an expandable distal section which can be positioned at a treatment site 34 within a lung or another target medium. In operation, the device is manipulated to the treatment site 34. RF energy, for example, is delivered through the energy delivering device and penetrates the surface of the lung tissue such that tissue is affected below the epithelial layer as well as on the surface of the lung tissue. The application of energy may cause a variety of structural and physiological effects which may result from the application of energy to the airway wall. For example, application of energy to the airway smooth muscle of an asthmatic patient can debulk or otherwise reduce the volume of smooth muscle. This reduced volume of smooth muscle increases the airway diameter for improved air exchange. Even small increases in the airway size can provide relief as the resistance to airflow varies inversely with approximately the fourth power of diameter.

Application of energy to an airway wall can also reduce inflammation in the inner lung tissue. Reducing inflammation and edema of the tissue surrounding the airway can increase the diameter of an airway. Inflammation and edema (accumulation of fluid) of the airway are chronic features of asthma. The inflammation and edema can be reduced by application of energy to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. The wound healing can also deposit collagen which improves parenchymal tethering.

Application of energy to an airway wall can also inhibit the release of inflammatory mediators in the airway wall which may serve as a stimulus for airway smooth muscle contraction. Therapy that reduces the production and release of inflammatory mediators can reduce smooth muscle contraction, inflammation of the airways, and edema. Examples of inflammatory mediators are cytokines, chemokines, and histamine. The tissues which produce and release inflammatory mediators include airway smooth muscle, epithelium, and mast cells. Thus, treatment of these structures with energy can reduce the ability of the airway structures to produce or release inflammatory mediators. The reduction in released inflammatory mediators will reduce chronic inflammation, thereby increasing the airway inner diameter, and may also reduce hyper-responsiveness of the airway smooth muscle.

Application of energy to an airway wall can also increase the airway diameter by damaging nerve tissue in the airways. This follows because a resting tone of smooth muscle is nerve regulated by release of catecholamines. Thus, by damaging or eliminating nerve tissue in the airways the resting tone of the smooth muscle is reduced, and the airway diameter is increased.

Application of energy to the airways may cause other physiological responses which result in increased diameters. It is to be understood, however, that the invention is not limited to a certain physiological response or process except where such a physiological response or process is a claim limitation in the appended claims.

As shown in FIG. 4, the present invention may be performed using a controller 32 and a device 30 through which it delivers energy to the target medium 34. A device 30 of the present invention should be of a size to access the bronchus or bronchioles of the human lung. The device may be sized to fit within bronchoscopes, preferably, with bronchoscopes having a working channel of 2 mm or less. The device may also include a steering member configured to guide the device to a desired target location. For example, this steering member may deflect a distal tip of the device in a desired direction to navigate to a desired bronchi or bronchiole.

Another aspect of the present invention is to treat more than one location. Several to many locations (e.g., reference numerals 31, 34 and 38) in the airways may be treated in order to reduce asthmatic symptoms. This can be accomplished by manipulating or positioning the expandable basket at a target site in the airways, expanding the expandable basket such that the energy transfer elements (e.g., the basket legs) contact the airway wall, and then delivering energy to the airway wall. The expandable basket is preferably collapsed and moved to another location and the process is repeated. This technique for applying energy at discrete locations can be repeated as many times as necessary to treat the asthmatic symptoms.

The present invention also includes applying energy continuously along an airway as an expanded basket is moved along the airway. Specifically, the basket may be deployed, energized, and then moved along the airway continuously to continually transfer energy to or from the airway wall as the basket is moved axially along the airway. The above described methods may also be used in combination with one another.

Figure 5:
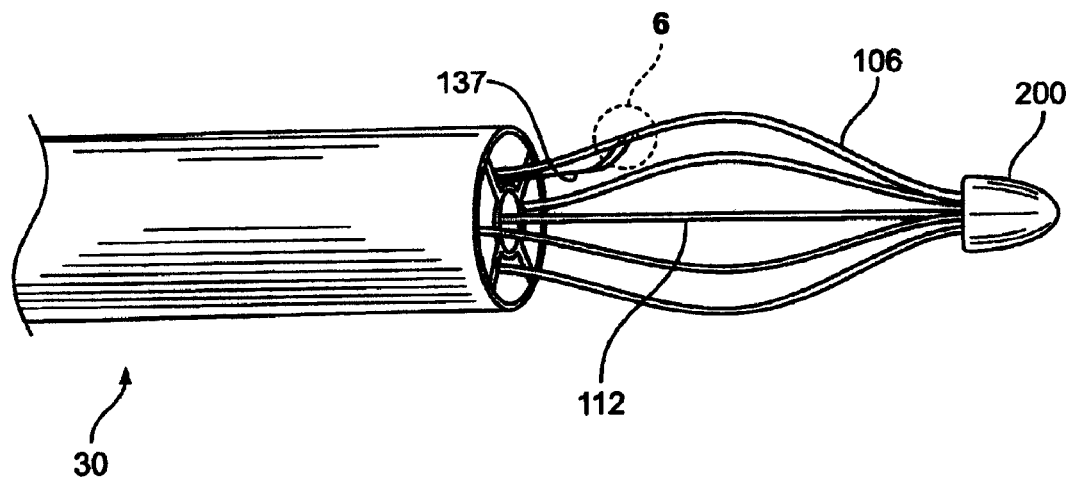
FIG. 5 is a partial view of an energy delivery device which can be used to carry out the method of the invention.

An exemplary partial view of an energy delivering device which may be used to perform the invention is shown in FIG. 5. The energy delivering apparatus 30 typically includes an elongate body having a proximal section and a distal section. The distal section features a radially expandable basket having a plurality of legs 106. The legs may be electrodes or have an active region defined by an insulated covering which contacts the medium to be treated. The basket is expanded with an actuator mechanism 112 which may be activated by a movable lever in a handle attached to the proximal end of the elongate body.

The invention may also include an atraumatic tip 200 to ensure that the invention does not injure airway tissue when it is placed into airways that are partially or completely closed. The tip may be formed of a flexible material and/or may be rounded to minimize trauma. Examples of energy delivering devices in accordance with the present invention are described in co-pending U.S. application Ser. No. 09/436,455 filed Nov. 8, 1999 which is hereby incorporated by reference in its entirety. Other examples of devices and methods which may be used in accordance with the present invention are found in the following U.S. patent application Ser. No. 09/095,323—Methods and Apparatus for Treating Smooth Muscles in the Walls of Body Conduits; Ser. No. 09/349,715—Method of Increasing Gas Exchange of a Lung; and Ser. No. 09/296,040—Devices for Modification of Airways By Transfer of Energy. The entirety of each of the aforementioned applications is hereby incorporated by reference. Another suitable energy device is described in International patent application no PCT/US00/28745.

The energy delivery device may further comprise a temperature detecting element. Examples of temperature detecting elements include thermocouples, infrared sensors, thermistors, resistance temperature detectors (RTDs), or any other apparatus capable of detecting temperatures or changes in temperature. The temperature detecting element is preferably placed in proximity to the expandable member.

Figure 6:
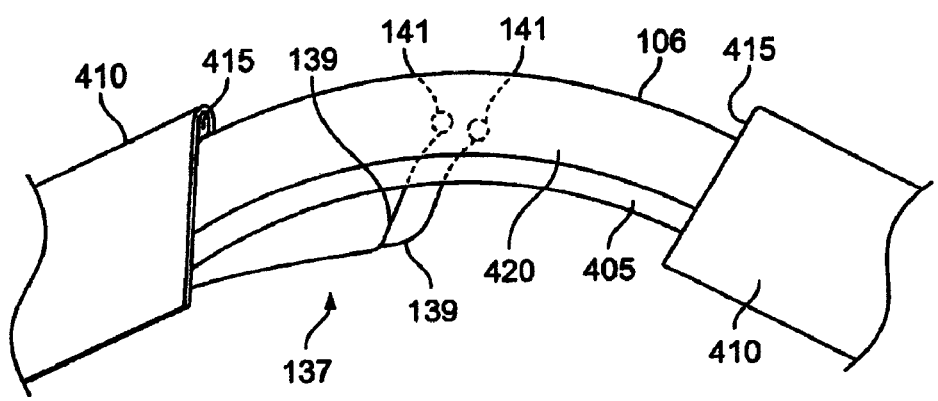
FIG. 6 is a partial view of a thermocouple attached to an energy delivering device in accordance with the invention.

FIG. 5 is a partial view of a variation of the energy delivery device having thermocouple 137 positioned about midway along basket leg 106. FIG. 6 is an enlarged partial view of the thermocouple 137 of FIG. 5 showing the leads 139 separately coupled on an inwardly-facing surface of the leg 106. Consequently, the basket leg itself is used as part of the thermocouple junction upon which the temperature measurement is based. The thermocouple junction is intrinsic to the basket leg. This configuration is preferred because it provides an accurate temperature measurement of tissue contacting the leg 106 in the vicinity of the thermocouple leads. In contrast, typical thermocouple configurations consist of a thermocouple junction offset or extrinsic to the basket leg. Thermocouple junctions offset or extrinsic to the basket leg do not measure temperature as accurately in certain applications as thermocouple junctions which are intrinsic to the basket leg.

An intrinsic thermocouple junction configuration is safer than an extrinsic thermocouple junction because, in the event one of the thermocouple leads separates from a basket leg, the intrinsic thermocouple junction becomes "open" and no thermocouple signal is produced. In contrast, when an extrinsic thermocouple junction separates from a basket leg a signal continues to be produced. The signal of a detached extrinsic thermocouple junction can be misleading because although a temperature reading continues to be produced, the temperature reading does not reflect the temperature at the point where the basket leg contacts the subject tissue. Accordingly, an intrinsic thermocouple junction having two leads separately attached to a basket leg is preferred.

FIG. 6 also shows basket leg 106 having an outer insulating material or coating 410. The boundaries 415 of the insulating material 410 define an uninsulated, active section of electrode leg 106 which delivers energy to the airway walls. Preferably, the insulating coating 410 is heat shrink tubing or a polymeric coating. However, other insulating materials may be used.

Various controllers may be used to carry out the invention. An example of an RF controller which may be used to carry out the invention is described in co-pending International Patent Application No. PCT/US01/32321, entitled "CONTROL SYSTEM AND PROCESS FOR APPLICATION OF ENERGY TO AIRWAY WALLS AND OTHER MEDIUMS" filed Oct. 17, 2001 incorporated herein by reference in its entirety.

The controller and power supply is configured to deliver enough energy to produce a desired effect in the lung. The power supply should also be configured to deliver the energy for a sufficient duration such that the effect persists. This may be accomplished by a time setting which may be entered into the power supply memory by a user.

The power supply or generator may also employ a number of algorithms to adjust energy delivery, to compensate for device failures (such as thermocouple detachment), to compensate for improper use (such as poor contact of the electrodes), and to compensate for tissue inhomogeneities which can affect energy delivery such as, for example, subsurface vessels, adjacent airways, or variations in connective tissue.

The power supply can also include circuitry for monitoring parameters of energy transfer: (for example, voltage, current, power, impedance, as well as temperature from the temperature sensing element), and use this information to control the amount of energy delivered. In the case of delivering RF energy, typical frequencies of the RF energy or RF power waveform are from 300 to 1750 kHz with 300 to 500 kHz or 450 to 475 being preferred. The RF power-level generally ranges from about 0-30 W but depends upon a number of factors such as the size and number of the electrodes. The controller may also be configured to independently and selectively apply energy to one or more of the basket leg electrodes.

A power supply may also include control modes for delivering energy safely and effectively. Energy may be delivered in open loop (power held constant) mode for a specific time duration. For example, a power setting of 8 to 30 Watts for up to 10 seconds is suitable and a power setting of 12 to 30 Watts for up to 5 seconds is preferred. For more permanent restructuring of the airways, a power setting of 8 to 15 Watts for 5 to 10 seconds is suitable. For mere temporary relief or enlargement of the airway, a power setting of 10 to 25 Watts for up to 3 seconds is suitable. With higher power settings, correspondingly lower time durations are preferred to limit collateral thermal damage.

Energy may also be delivered in temperature control mode, with output power varied to maintain a certain temperature for a specific time duration. For example, energy may be delivered for up to 20 seconds at a temperature of 55 to 80 degrees C., and more preferably, energy is delivered up to 10 seconds at a temperature in the range of 60 to 70 degrees C. For more permanent restructuring of the airways, energy is delivered for 5 to 10 seconds at a temperature in the range of 60 to 70 degrees C. For mere temporary relief or enlargement of the airway, energy is delivered for up to 5 seconds at a temperature of 55 to 80 degrees C. Additionally, the power supply may operate in impedance control mode.

The operator may start at low values of power, temperature and time, and treat until the desired effect (for example, airway diameter increasing or tissue blanching) is acutely observed, raising the power, temperature or time as needed.

Notably, the methods of the invention may be performed while the lung is experiencing natural symptoms of reversible obstructive pulmonary disease. One such example is where an individual, experiencing an asthma attack, or acute exacerbation of asthma or COPD, undergoes treatment to improve the individual's ability to breath. In such a case, the treatment provides immediate relief for (i.e., "rescues") the patient.

All of the features disclosed in the specification (including any accompanying claims, abstract and drawings), and/or all of the steps of any method or process disclosed, may be combined in any combination, except combinations where at least some of such features and/or steps are mutually exclusive.

Each feature disclosed, in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method for treating asthma comprising:
   advancing an energy delivery device into an airway of a lung;
   deploying the energy delivery device so that a plurality of electrodes contact a wall of the airway; and
   applying energy to the airway wall such that the airway wall is altered so an ability of the airway to contract or constrict is reduced.

2. A method for treating asthma comprising:
   positioning a bronchoscope into an airway of a lung;
   advancing an energy delivery device into the bronchoscope until a distal portion of the device projects from the bronchoscope at a treatment site within the airway; and
   delivering energy to the treatment site such that airway tissue is altered so an ability of the airway to contract or constrict is reduced.

3. A method for treating asthma comprising:
   positioning an energy delivery device into an airway of a lung; and
   delivering radio frequency energy to a wall of the airway for a period of 1-120 seconds such that the airway wall is altered so an ability of the airway to contract or constrict is reduced.

4. A method for treating asthma comprising:
   positioning an energy delivery device into an airway of a lung; and
   delivering radio frequency energy to a wall of the airway at a predetermined temperature in a range from about 40 degrees Celsius to about 95 degrees Celsius such that the airway wall is altered so an ability of the airway to contract or constrict is reduced.

5. A method for treating asthma comprising:
   positioning an energy delivery device into an airway of a lung; and
   delivering radio frequency energy to a wall of the airway at a power level of 1-10 watts such that the airway wall is altered so an ability of the airway to contract or constrict is reduced.

6. A method for treating asthma comprising:
   positioning an energy delivery device within an airway of a lung;
   delivering radio frequency energy to a wall of the airway such that the airway wall is altered so an ability of the airway to contract or constrict is reduced; and
   monitoring temperature or impedance in airway tissue.

7. A method for treating asthma comprising:
   positioning an energy delivery device within a lung; and
   delivering energy to the lung in stages by treating different regions of the lung at different times, wherein energy delivery alters the airways so an ability of the airway to contract or constrict is reduced.

* * * * *

UNITED STATES PATENT AND TRADEMARK OFFICE
CERTIFICATE OF CORRECTION

PATENT NO. : 7,740,017 B2
APPLICATION NO. : 11/117905
DATED : June 22, 2010
INVENTOR(S) : Danek et al.

It is certified that error appears in the above-identified patent and that said Letters Patent is hereby corrected as shown below:

Title Page, Item (56) on page 4, in column 1, under "Other Publications", line 17, delete "Jerse" and insert -- Jersey --, therefor.

Title Page, Item (56) on page 4, in column 2, under "Other Publications", line 12-13, delete "Evaluation" and insert -- Evaluating --, therefor.

Title Page, Item (56) on page 4, in column 2, under "Other Publications", line 21, delete "Invervention" and insert -- Intervention --, therefor.

Title Page, Item (56) on page 4, in column 2, under "Other Publications", line 28, delete "Medicial" and insert -- Medical --, therefor.

Title Page, Item (56) on page 4, in column 2, under "Other Publications", line 50, delete "Pshychological" and insert -- Psychological --, therefor.

In column 4, line 4, delete "121" and insert -- 12 --, therefor.

In column 4, line 5, delete "quit" and insert -- quite --, therefor.

Signed and Sealed this

Seventh Day of September, 2010

David J. Kappos
*Director of the United States Patent and Trademark Office*